United States Patent [19]

Van Geem et al.

[11] 4,137,259

[45] Jan. 30, 1979

[54] CATALYTIC GAS PHASE OXIDATION OF TOLUENE TO BENZALDEHYDE AND/OR BENZOIC ACID

[75] Inventors: Paul C. Van Geem; Antonius J. J. M. Teunissen, both of Geleen, Netherlands

[73] Assignee: Stamicarbon, B.V., Geleen, Netherlands

[21] Appl. No.: 811,321

[22] Filed: Jun. 29, 1977

[30] Foreign Application Priority Data

Jul. 9, 1976 [NL] Netherlands ......................... 7607598

[51] Int. Cl.² ........................... C07C 51/33; B01J 29/16
[52] U.S. Cl. ...................................... 562/415; 252/456
[58] Field of Search ...................................... 260/524 R

[56] References Cited

U.S. PATENT DOCUMENTS

| | | | |
|---|---|---|---|
| 2,749,363 | 6/1956 | Williamson | 260/524 |
| 3,170,768 | 2/1965 | Baldwin | 260/524 |
| 3,485,876 | 12/1969 | Mond | 260/524 |

Primary Examiner—A. Siegel
Attorney, Agent, or Firm—Cushman, Darby & Cushman

[57] ABSTRACT

A catalyst mass of silver vanadate and iron vanadate, optionally also including at least one rare earth metal vanadate, is used in the vapor phase oxidative conversion of toluene to benzaldehyde and/or benzoic acid using oxygen or ozone and steam according to the disclosed process. Catalyst activity and selectivity are improved.

8 Claims, No Drawings

CATALYTIC GAS PHASE OXIDATION OF TOLUENE TO BENZALDEHYDE AND/OR BENZOIC ACID

BACKGROUND OF THE INVENTION

The present invention relates to the catalytic gas phase oxidation of toluene with a gas containing molecular oxygen in the presence of a silver vanadate catalyst which conversion yields benzaldehyde, benzoic acid or both products.

A process for the catalytic oxidation of toluene with molecular oxygen, including ozone, is described in British Patent Specification 1,164,316, which is hereby incorporated by reference. According to this reference catalysts based on silver vanadate show, in addition to a reasonable degree of activity, a particularly good selectivity, that is only a small portion of the oxidized amount of toluene changes over into valueless carbon dioxide, while the remainder consists principally of the desired benzaldehyde and benzoic acid products.

It is also known to catalytically oxidize toluene in the vapor phase with oxygen or ozone to benzaldehyde using as the catalyst a mixture of silver vanadate with lead vanadate or silver arsenate. This catalyst system suppresses both the formation of benzoic acid and degradation to carbon dioxide and is described in commonly assigned U.S. Pat. No. 3,485,876, the disclosure of which is hereby incorporated by reference. As explained in this patent selectivity of the catalyst determines the quality of the product, such as the percentage of the desired product. The activity of a catalyst determines the rate of conversion, that is the percentage of starting material converted into the product.

DETAILED DESCRIPTION OF THE INVENTION

We have now found and hereby disclose that, in relation to the gas phase oxidation of toluene with oxygen or ozone, the catalyst based on silver vanadate can still be improved by providing that the catalyst also contain iron vanadate in addition to silver vanadate. The improvement obtained through the presence of iron vanadate in the catalyst mass consists, while the catalyst selectivity remains approximately the same, in the activity of the catalyst increasing considerably. This increase in catalyst activity was not to be expected seeing that a catalyst based on iron vanadate, as compared with a catalyst based on silver vanadate, in the oxidation of toluene with oxygen or ozone under comparable conditions is less suitable from a standpoint both of catalyst activity and catalyst selectivity. This observation is illustrated by the comparative examples that follow.

An increase in the activity of a catalyst based on the combination silver vanadate with iron vanadate becomes clearly perceptible even when the combination contains relatively small quantities of iron as compared to the amount of silver. We have found that a catalyst in which the atomic ratio of iron to silver is as small as 1:5 already can be used to advantage.

The most demonstrable improvement in activity is obtained if the atomic iron-to-silver ratio amounts to about 1:2, but also catalyst systems of the type here disclosed having an atomic iron-to-silver ratio of 2:1 still show a higher activity than a catalyst based only on silver vanadate. We prefer that the atomic iron-to-silver ratio be between 5:1 to about 0.2:1.

In addition to silver vanadate and iron vanadate the catalyst of our invention preferably also contains a vanadate of one or more of the so-called rare earth metals. We have found that such additions cause the activity of the catalyst to increase considerably further. The activity of a catalyst of this kind (silver vanadate plus iron vanadate plus rare earth metal vanadate) is also substantially higher than that of a catalyst consisting solely of silver vanadate and a vanadate of one or more of the rare earth metals. The group of the rare earth metals specifically contemplated herein comprises the elements having the atom numbers 57 to 71 inclusive as well as scandium and yttrium. For preference and convenience the rare earth metal or metals employed are one of the more readily available rare earth metals, such as scandium, yttrium, lanthanum, cerium or 'didymium' (which is a mixture of praseodymium and neodymium). The atomic rare earth-to-silver ratio is preferably between about 5:1 and about 0.2:1, most preferably about 1:2.

The various components of the catalyst should be mixed well. Preferably mixing is carried out by coprecipitation of the catalytic components, for instance by mixing an aqueous ammonium vanadate solution and an iron nitrate or iron chloride solution and optionally a solution of a salt of the desired rare earth metal or metals. The catalyst components are preferably applied to a carrier material such as aluminium oxide or silicon oxide.

In the oxidation of toluene less than the stoichiometric amount, or only a small excess of that amount, of oxygen or ozone is employed so as to prevent the formation of large amounts of the toluene being oxidized into carbon dioxide and water. An optimum result is usually obtained at a volumetric toluene vapor-to-oxygen ratio of between about 2:1 to about 1:2.

Further, to improve the selectivity of the oxidation reaction it is desirable that in addition to toluene, the reaction mixture should also contain a considerable quantity of steam. The volumetric toluene-to-steam ratio may e.g. be from 0.05:1 to 2:1. Optimum results are usually obtained at a volumetric toluene-to-steam ratio of about 0.5:1. When using volumetric toluene-to-steam ratios higher than 0.5:1 we have found that there is an increase in the formation of undesirable by-products, such as tolyl benzaldehyde and ditolyl, and of the formation of carbon dixoxide. On the other hand when the volumetric toluene-to-steam ratios are lower than 0.5:1 while such ratios certainly have no detrimental influence on the activity and the selectivity of the catalyst, when using such a process on an industrial scale there is no point in using more steam than is otherwise necessary, as this is only disadvantageous from an economical point of view. Thus, for practical and economic reasons the toluene-to-steam ratio is usually maintained at about 0.5:1.

The space velocities of the gaseous mixture passed over the catalyst used in the catalytic oxidation of toluene may be varied between wide limits. At a toluene content of about 10% by volume in the gaseous mixture, space velocities of, say, 750 to 10,000 liters of gaseous mixture per liter of catalyst per hour can be employed without adversely affecting the activity, selectivity or both of the catalyst. It is generally true that a high space velocity has the advantage of a higher daily production, even if the degree of conversion is slightly lower than is the case at a lower space velocity.

The oxidation of toluene with oxygen or ozone in the presence of a catalyst containing silver vanadate with iron vanadate and optionally including a rare earth metal vanadate as the catalytically active components thereof is carried out at a temperature in the range of about 300° C. to about 500° C. and preferably in the range of about 350 to about 400° C.

The products obtained in the oxidation of toluene with oxygen or ozone in the presence of a catalyst containing the combination silver vanadate and iron vanadate and optionally the vanadate of one or more of the rare earth metals, contain a very high proportion of benzaldehyde and benzoic acid.

The benzaldehyde content using the novel catalyst systems here disclosed may be about 95% by weight of the total quantity of aldehydes produced, while about 80% of the acids formed from the toluene is present in the form of benzoic acid.

Oxidation products formed by the process of the present invention are separated from each other and from the non-oxidized toluene in the usual manner such as by condensation and distillation. The non-oxidized toluene that is so recovered is again passed over the catalyst with steam and oxygen. The invention will now be further illustrated with reference to the following examples in which comparative experiments A, B and C relate to the testing of a catalyst system based on silver vanadate, iron vanadate, and silver vanadate plus the vanadate of one or more of the rare earth metals, respectively, in the gas phase oxidation of toluene with oxygen. The examples 1 and 2 relate to the testing of a catalyst system according to the present invention. Unless otherwise indicated all parts and percentages are by weight.

Comparative examples A1 and A2

A catalyst mass consisting of 20% by weight of silver vanadate and 80% by weight of silica ($SiO_2$) as the carrier material was prepared by suspending silica in an aqueous solution of ammonium metavanadate, subsequently adding a silver nitrate solution to this suspension, filtering off the resulting precipitate, drying it and subjecting it to heat treatment at 450° C.

Toluene was oxidized with this catalyst, in which the atomic Ag:V ratio amounted to approximately 1:1. On an hourly basis a mixture of 2.1 Nl (Nl stands for normal liter) of toluene vapor, 2.4 Nl of oxygen, 11.8 Nl of nitrogen and 10.4 Nl of steam was passed over 20 ml of the catalyst so prepared. The catalyst mass was kept at a temperature of 382° C. Under these conditions 21% of the toluene was converted.

Of the toluene supplied 7% was converted into benzaldehyde, 6% into benzoic acid, 1% into benzene, and 3.5% into carbon monoxide and carbon dioxide.

The experiment was repeated with a similarly prepared catalyst consisting of 40% by weight of silver vanadate and 60% by weight of silica. The atomic Ag:V ratio again amounted to approximately 1:1. The hourly amounts of toluene vapor, oxygen, nitrogen and steam passed over 20 ml of the catalyst were 2.1 Nl, 2.0 Nl, 13.0 Nl and 11.0 Nl, respectively. Under these conditions 24% of the toluene was converted.

Of the toluene supplied 7% was converted into benzaldehyde, 9% into benzoic acid, 1% into benzene, and 5% into carbon monoxide and carbon dioxide.

Comparative example B

A catalyst mass consisting of 20% by weight of iron vanadate and 80% of silica as carrier material was prepared by suspending silica in an aqueous solution of ammonium metavanadate, subsequently adding an iron nitrate solution to this suspension, and filtering off the resulting precipitate, then drying it and subjecting it to heat treatment at 450° C.

Toluene was oxidized with this catalyst, in which the atomic Fe:V ratio was approximately 1:3. Under the same conditions as in comparative experiment A1, a toluene conversion of 26% was reached.

Of the toluene supplied 3% was converted into benzaldehyde, 7% into benzoic acid, 0.2% into benzene, and 11% into carbon monoxide and carbon dioxide.

Comparative example C

A catalyst mass consisting of 20% by weight of silver vanadate, 20% by weight of cerium vanadate and 60% by weight of silica as a carrier was prepared by adding a solution of silver nitrate and cerium nitrate to a suspension of silica in an ammonium metavanadate solution, then filtering off the precipitate, drying it and subjecting it to heat treatment at 450° C.

This catalyst mass, in which the atomic ratio of Ag:Ce:V was about 2:1:5, was used to oxidize toluene. On an hourly basis a mixture of 2.1 Nl of toluene vapor, 0.9 Nl of oxygen, 8.3 Nl of nitrogen, and 10.9 Nl of steam was passed over 20 ml of the catalyst. At a reaction temperature of 355° C. a toluene conversion of 16% was reached.

Of the toluene supplied, 5% was converted into benzaldehyde, 6.5% into benzoic acid, 0.3% into benzene, and 2.3% into carbon monoxide and carbon dioxide.

EXAMPLE 1

A catalyst mass consisting of 20% by weight of silver vanadate, 20% by weight of iron vanadate and 60% by weight of silica as a carrier material was prepared by suspending silica in an aqueous ammonium metavanadate solution, by subsequently adding a solution of silver nitrate and iron nitrate to this suspension, then filtering off the resulting precipitate, drying it and subjecting it to heat treatment at 450° C. Toluene was oxidized with this catalyst, in which the atomic ratio of Ag:Fe:V was approximately 2:1:5. Under the same conditions as in Comparative Experiment A1 a toluene conversion of 34% was reached.

Of the toluene supplied 7% was converted into benzaldehyde, 11% into benzoic acid, 2% into benzene, and 9% into carbon monoxide and carbon dioxide.

EXAMPLE 2

A catalyst mass consisting of 20% by weight of silver vanadate, 20% by weight of cerium vanadate, 20% by weight of iron vanadate and 40% by weight of silica as a carrier was prepared by adding a solution containing silver nitrate, cerium nitrate and iron nitrate to a suspension of silica in an ammonium metavanadate solution, by filtering off the precipitate, drying it and subjecting it to heat treatment at 450° C.

This catalyst mass, in which the atomic ratio of Ag:Ce:Fe:V was approximately 2:1:1:8, was used to oxidize toluene. On an hourly basis a mixture of 2.1 Nl of toluene vapor, 2.0 Nl of oxygen, 10.0 Nl of nitrogen and 10.6 Nl of steam was passed over 20 ml of this catalyst.

At a reaction temperature of 361° C. a toluene conversion of 25% was reached.

Of the toluene supplied 4% was converted into benzaldehyde, 10% into benzoic acid, 0.6% into benzene, and 6% into carbon monoxide and carbon dioxide.

The test results of the above examples are conveniently summarized in the following table, in which GHSV stands for "Gas Hourly Space Velocity", the specific space velocity which is expressed in Nl of feed per l of catalyst per hour.

| | catalyst | GHSV | temperature (° C.) | total conversion (%) | conversion into benzaldehyde and benzoic acid (%) |
|---|---|---|---|---|---|
| Comparative experiment A1 | silver vanadate/SiO$_2$ | 1335 | 382 | 21 | 13 |
| Comparative experiment A2 | silver vanadate/SiO$_2$ | 1335 | 382 | 24 | 16 |
| Comparative experiment B | iron vanadate/SiO$_2$ | 1335 | 382 | 26 | 10 |
| Example 1 | silver iron vanadate/SiO$_2$ | 1335 | 382 | 34 | 18 |
| Comparative experiment C | silver cerium vanadate/SiO$_2$ | 1110 | 355 | 16 | 11.5 |
| Example 2 | silver cerium iron vanadate/SiO$_2$ | 1235 | 361 | 25 | 14 |

These examples show that in the process according to the invention and using the novel catalyst masses here disclosed a higher production of benzaldehyde and benzoic acid is achieved while using essentially the same amount of catalytically active material than as is used in prior procedures. As an added advantage, owing to the higher toluene conversion per pass of reaction mixture over the catalyst mass, the costs of processing and recirculating unconverted toluene are lower. This feature of the invention is particularly attractive in the commercial practice of the present invention.

What is claimed is:

1. In a process for the vapor-phase catalytic oxidation of toluene with oxygen or ozone to benzaldehyde and benzoic acid at a temperature between about 300° C. and about 500° C. in the presence of a silver vanadate catalyst, the improvement consisting essentially in carrying out said oxidation reaction in the presence of a catalyst mass composed of silver vanadate and iron vanadate as the catalytically active components.

2. The process of claim 1 wherein the atomic ratio of silver to iron in said catalyst mass is in the ratio of about 5:1 to about 0.2:1.

3. The process of claim 1 wherein the catalyst mass is prepared by co-precipitation silver vanadate and iron vanadate from an aqueous solution of ammonium metavanadate.

4. The process of claim 1 wherein the reaction is conducted in the presence of steam present in an amount such that the volumetric ratio of toluene to steam is from 0.05:1 to 2:1.

5. The process of claim 4 wherein the volumetric ratio of toluene to steam is about 0.5:1.

6. In a process for the vapor-phase catalytic oxidation of toluene with oxygen or ozone to benzaldehyde and benzoic acid at a temperature between about 300° C. and about 500° C. in the presence of a silver vanadate catalyst,
the improvement consisting essentially in carrying out said oxidation reaction in the presence of a catalyst mass composed of silver vanadate with iron vanadate and a vanadate of at least one rare earth metal as the catalytically active components.

7. The process of claim 6 wherein the atomic ratio of silver to iron is in the ratio of about 5:1 to about 0.2:1 and the atomic ratio of silver to said rare earth metal is in the ratio of about 5:1 to about 0.2:1 in said catalyst mass.

8. The process of claim 6 wherein the catalyst mass is prepared by co-precipitation of silver vanadate, iron vanadate and said rare earth metal vanadate from an aqueous solution of ammonium metavanadate.

* * * * *